(12) United States Patent
Schulz

(10) Patent No.: US 7,976,175 B2
(45) Date of Patent: Jul. 12, 2011

(54) RING LAMP FOR ILLUMINATING A DELIMITED VOLUME AND THE USE THEREOF

(75) Inventor: Jan Schulz, Bremerhaven (DE)

(73) Assignee: Stiftung Alfred-Wegener-Institut Fuer Polar- und Meeresforschung, Bremerhaven (DE)

( * ) Notice: Subject to any disclaimer, the term of this patent is extended or adjusted under 35 U.S.C. 154(b) by 271 days.

(21) Appl. No.: 12/090,812

(22) PCT Filed: Sep. 15, 2006

(86) PCT No.: PCT/DE2006/001657
§ 371 (c)(1),
(2), (4) Date: Sep. 5, 2008

(87) PCT Pub. No.: WO2007/045200
PCT Pub. Date: Apr. 26, 2007

(65) Prior Publication Data
US 2009/0016058 A1    Jan. 15, 2009

(30) Foreign Application Priority Data
Oct. 19, 2005 (DE) .......................... 10 2005 050 722

(51) Int. Cl.
*G03B 15/02* (2006.01)
(52) U.S. Cl. ..... 362/11; 362/244; 362/268; 362/249.14; 362/336; 362/338
(58) Field of Classification Search .................. 362/11, 362/268, 244, 246, 249.14, 336, 338
See application file for complete search history.

(56) References Cited

U.S. PATENT DOCUMENTS

| 4,380,392 A | | 4/1983 | Karabegov et al. | |
|---|---|---|---|---|
| 4,893,223 A | | 1/1990 | Arnold | |
| 5,092,675 A | | 3/1992 | Sommer | |
| 5,396,333 A | | 3/1995 | Aleshin et al. | |
| 5,580,163 A | * | 12/1996 | Johnson, II | 362/285 |
| 5,690,417 A | * | 11/1997 | Polidor et al. | 362/244 |
| 5,897,195 A | * | 4/1999 | Choate | 362/33 |
| 6,122,053 A | * | 9/2000 | Zwaal | 356/338 |

(Continued)

FOREIGN PATENT DOCUMENTS
DE   221861   5/1985
(Continued)

*Primary Examiner* — Jong-Suk (James) Lee
*Assistant Examiner* — Mark Tsidulko
(74) *Attorney, Agent, or Firm* — Leydig, Voit & Mayer, Ltd.

(57) ABSTRACT

A ring lamp includes a light source having a first hollow cylinder with a lighting device disposed therein. The light source has an emitting surface with a light-emitting direction oriented toward an axis of the hollow cylinder. The lamp also includes a light directing device configured to direct light emission. The light directing device includes a lens system having a lens formed as a second hollow cylinder and configured to focus light into a radial plane which is orthogonal to the axis. The lens system has a ring-shaped aperture diaphragm disposed centrally in an optical path of the light emission behind the lens. The emitting surface of the light source and the lens system have a same length, are coaxial and axially aligned with each other. A radial surface which is defined by an inner radius of the lens system and the length of the lens system spans a delimited volume.

19 Claims, 4 Drawing Sheets

U.S. PATENT DOCUMENTS

| | | | |
|---|---|---|---|
| 6,238,060 B1 * | 5/2001 | Bourn et al. | 362/216 |
| 6,533,429 B2 | 3/2003 | Yoneda et al. | |
| 7,357,529 B2 * | 4/2008 | Choate et al. | 362/239 |
| 2006/0018113 A1 * | 1/2006 | Upmeyer | 362/158 |

FOREIGN PATENT DOCUMENTS

| | | |
|---|---|---|
| DE | 232552 | 1/1986 |
| DE | 29813109 | 10/1998 |
| DE | 19724364 | 12/1998 |
| DE | 19736172 | 2/1999 |
| DE | 19837797 | 6/1999 |
| DE | 29921159 | 2/2000 |
| DE | 10129972 | 1/2003 |
| DE | 10211768 | 10/2003 |
| DE | 10356384 | 6/2005 |
| EP | 1072884 | 1/2001 |
| EP | 1411290 | 4/2004 |
| JP | 11002598 | 1/1999 |

* cited by examiner

RING LAMP FOR ILLUMINATING A DELIMITED VOLUME AND THE USE THEREOF

CROSS REFERENCE TO PRIOR RELATED APPLICATIONS

This is a U.S. National Phase application under 35 U.S.C. §371 of International Application No. PCT/DE2006/001657, filed on Sep. 15, 2006, and claims the benefit of German Patent Application No. 10 2005 050 722.0, filed on Oct. 19, 2005. The International Application was published in German on Apr. 26, 2007 as WO 2007/045200 A1 under PCT Article 221(2).

FIELD

The invention relates to a ring lamp having a light source configured as a hollow cylinder with an illuminating means or lighting device and having a device to direct the light emission, whereby the light source has an emitting surface with a light-emitting direction oriented towards the axis of the hollow cylinder.

BACKGROUND

Ring lamps of this type are employed, for example, in camera objectives used for macrophotography, as operating theater illumination in medicine or else for transmitted-light or reflected-light illumination in optical microscopy. In this context, such a ring lamp is arranged concentrically to the optical axis of the image-forming optical system. Therefore, in contrast to spot illumination, the object to be imaged is illuminated without any shadows. Shadowless, uniform and intense illumination is also needed in the field of particle detection in currents, but only within a delimited volume, as a result of which only the particles that enter the illuminated area with the current are observed.

There are various illumination devices in the field of particle detection. East German patent application DD 232 552 A1 describes a device to count and classify dispersed particles in liquids having volume to be measured that is spatially delimited by a measuring cell, a laser beam serving to illuminate the volume to be measured, whereby the beam focus lies in the center of the volume to be measured, so that the detected volume to be measured is reduced to a single point. The volume to be measured is restricted by the configuration of the measuring cell in such a way that every time only one particle is situated in the light focus and its scatter in the laser light is then measured. East German patent application DD 221 861 A1 describes an illumination device for generating a two-dimensional light strip for pattern recognition and identification of workpieces in an industrial setting. For this purpose, a linear light source is used whose beams are directed through a blade diaphragm and bundled by a cylindrical lens onto the object that is to be recognized. Contrast adjustment in the imaging system then creates and analyzes a sharp black-and-white image of the strip that is being illuminated. A reflector can be installed behind the light source for purposes of obtaining a higher light yield. Moreover, German utility model DE 298 13 109 U1 describes an illumination device for generating a long, narrow light band having two-dimensional characteristics. Here, the light from several lamps in a narrow housing with a first individual lens for each lamp and with a second, shared lens forms a narrow beam focused onto a line at a selectable distance. The light yield is approximately a function of the emitting angle and is thus very small. German patent specification DE 197 36 172 B4 describes a device for analyzing particles dispersed in a flowing liquid that works with diaphragms whose edges are curved like a hyperbola and thus, under illumination, these edges define a three-dimensional volume to be measured that has a known depth of field shaped like a truncated cone with curved edges. In the associated method, particles having a defined travel time in the volume to be measured are evaluated. The illumination device is arranged parallel to the detector, the detection signal is deflected out of the volume to be measured by a prism.

Prior-art video plankton recorders (VPR) utilize punctiform or linear light sources and individual spherical or cylinder lenses for the collimation. In large-scale applications, strong halogen systems are also used. These devices, however, entail the problem that no sharp optical delimitation of the volume to be measured can be created and the depth of field in the volume to be measured is adjusted employing complex software, which accounts for a high degree of imprecision of the estimated volume when used in the small-scale realm of plankton observation.

The ring lamp for shadowless reprophotography described in German utility model DE 299 21 150 U1 is a camera lamp. In this publication, which includes technical background for the present invention, a commercially available ring fluorescent lamp is employed as the illumination means. It emits its light uniformly to all sides, in other words, also towards the inside in the direction of the axis of the light source. Here, a device for directing the light emission is present in the form of a device that primarily changes the incidence of light onto the object to be illuminated in that the illumination means is raised or lowered. Furthermore, German patent application DE 102 11 768 A1 describes a ring lamp that is viewed in the present invention as being the closest state of the art. This publication discloses a light source consisting of a ring of light diodes for white light and configured as a flat hollow cylinder, the emitting direction of said light source being oriented inwards onto the axis of the hollow cylinder. Owing to a split construction, the diameter of the first ring that carries the light diodes can be changed relative to a stationary second ring. As a result of the fact that the lower end of the flexible, circularly curved mounting plate that carries the diodes is arranged in the stationary second ring and its upper end is arranged in the variable first ring, any change in the diameter of the first ring changes the angle of the light emission relative to the axis of the ring lamp. This device serves to optimize a shadowless illumination of several stationary objects that are to be imaged. The described device for directing the light emission, however, cannot illuminate a strictly delimited volume. Since the light is only delimited by the edges—whose dimensions are not defined—of the two rings that can be moved with respect to each other, it is freely emitted and thus spans a double conically shaped volume that is unsharply delimited towards the top and bottom and that has scatter areas that extend considerably beyond this.

SUMMARY

In an embodiment, the present invention provides a ring lamp including a light source having a first hollow cylinder with a lighting device disposed therein. The light source has an emitting surface with a light-emitting direction oriented toward an axis of the hollow cylinder. The lamp also includes a light directing device configured to direct light emission. The light directing device includes a lens system having a lens formed as a second hollow cylinder and configured to focus light into a radial plane which is orthogonal to the axis. The lens system includes a ring-shaped aperture diaphragm disposed centrally in an optical path of the light emission behind the lens. The emitting surface of the light source and the lens system have a same length, are coaxial and axially aligned with each other. A radial surface which is defined by an inner radius of the lens system and the length of the lens system spans a delimited volume.

BRIEF DESCRIPTION OF THE DRAWINGS

The invention will be described in greater detail with respect to the following exemplary embodiment and the drawings, in which.

DETAILED DESCRIPTION

Figure 1:
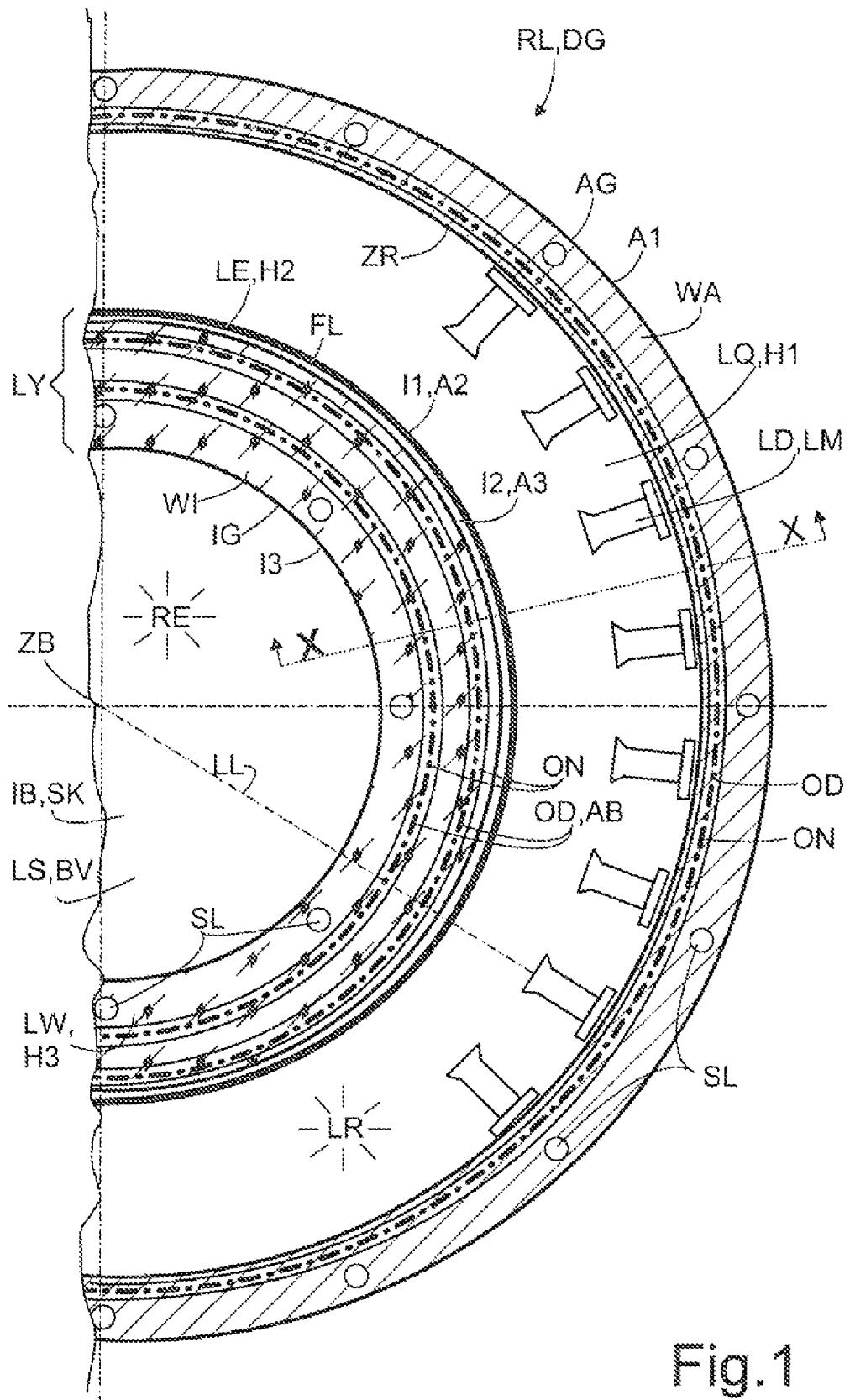
FIG. 1 shows a top view of a ring lamp without the top cover.

An aspect of the present invention is to provide a ring lamp which is capable of providing a particularly bright illumination of a volume that is strictly delimited in all three spatial dimensions. In this context, the ring lamp may be simple, it may be sturdy in terms of its structure and its handling, and it may be inexpensive to produce. Thus, in an embodiment, the present invention includes a device to direct the light emission that is formed by a lens system having at least one lens—configured as the other hollow cylinder—that focuses into a radial plane positioned orthogonally to the axis of the hollow cylinder that forms the light source, and having a ring-shaped aperture diaphragm centrally arranged in the optical path behind the one focusing lens, and that the emitting surface of the light source and the lens system have the same length and are arranged so as to be axis-congruent or coaxial and length-congruent relative to each other, whereby a radial surface determined by the inner radius of the lens system and the length of the lens system span a strictly delimited volume.

In an embodiment of ring lamps in devices employed for particle detection, for example, video plankton recorders (VPR), the generated disk of light is well-suited for the optical evaluation of particles passing through it in a dark or slightly illuminated environment if the generated disk of light is sharply delimited and not much thicker than the largest object to be imaged and if light scatter outside of the disk of light is avoided. The ring lamp according to the invention has an illumination means or lighting device that can be arranged so as to be uniformly distributed over a light source configured as a hollow cylinder. The emitting direction of the light source is towards the inside, perpendicular to the axis of the hollow cylinder, and thus aligned so as to coincide with the radial planes that are oriented orthogonally to the axis of the hollow cylinder. Thanks to this arrangement, it is achieved that the main luminous flux directly illuminates the interior of the hollow cylinder and only a very small scatter fraction thereof leaves this space spanned by the cross section and length of the hollow cylinder. Therefore, in an embodiment, a strictly delimited three-dimensional volume can be observed. This all-around arrangement of the illumination means achieves a virtually uniform and shadowless illumination of the objects located in the volume.

In accordance with an embodiment of the ring lamp according to the invention in video plankton recorders, the length of the hollow cylinder can be configured to be especially small, so that one can speak of a thin, circular disk of light. Plankters passing through along with the current are abruptly very brightly illuminated and they can be recorded by a camera system located at a distance that does not interfere with the current. Subsequently, the plankters are once again darkened without any transitions, thus avoiding undefined edge areas. With a precise focus onto the thin disk of light, non-illuminated plankters located between the camera and the disk of light as well as behind the disk of light will only have a slight damping effect on the imaging. The thinner the disk of light is, the less light is scattered towards the outside by the plankters passing through and reflected from the plankters that are still or once again un-illuminated in a manner detrimental to the imaging. The minimum thickness of the disk of light depends, on the one hand, on the possible construction-related circumstances and on the flow rates to be expected and, on the other hand, on the size of the plankters to be imaged, which may be completely in the light, at least for a brief period of time, whereby the requisite illumination and processing times as well as the depth of field for the camera also constitute additional parameters. In order to improve the imaging quality, the illumination means can also flash with a further heightened luminous flux.

The emission of the illumination means of the light source can be focused into a horizontal optical path for a disk of light that is strictly delimited in the length of the hollow cylinder. For this purpose, in a refinement of the ring lamp according to the invention, the one focusing lens may be configured as a Fresnel lens. Fresnel lenses or, to put it more precisely, Fresnel stepped lenses, are optical lenses that were originally developed for lighthouses. They allow the construction of large lenses having a short focal length and without the weight and volume of conventional lenses. The reduction of the volume in the case of Fresnel lenses is achieved by dividing the lens into a set of concentric annular zones. In each of these zones, the thickness is reduced in comparison to a conventional lens, so that the Fresnel lens acquires several annular rings that have the same curvature as each section of the original lens. Since light is only refracted at the surface of a lens, the angle of refraction is not dependent on the thickness, but rather, only on the angle between the two surfaces of a lens. This is why the Fresnel lens retains its optical properties, although the image quality is somewhat compromised by the stepped structure. Fresnel lenses are employed where the weight or the dimensions are a decisive factor and a reduced imaging quality can be tolerated. Examples are navigation lights or lighthouses. Fresnel lenses can be compression molded out of plastic and are then used in overhead projectors, automobile rear window lights and for simple hand-held magnifying glasses. When it comes to the ring lamp according to the present invention, another embodiment includes a Fresnel lens configured as a flexible film. Since the Fresnel lens compression molded as a film is very thin, it can be bent and adapted to the inner radius of the hollow cylinder that constitutes the light source. If the focal length of the Fresnel lens is configured in such a way that it is the same as the distance between the light diodes and the Fresnel lens, the light beams of the light diodes are deflected out of the Fresnel lens precisely into the radial plane of the hollow cylinder, as a result of which the thickness of the disk of light is determined with maximum utilization of the luminous flux supplied by the light diodes. The distance can also be varied in order to attain other scatter effects.

Another embodiment of the ring lamp according to the invention includes a lens system having another focusing lens that is configured as a third, smooth-walled, unstructured hollow cylinder having the same length as the one focusing lens and that is arranged so as to be axis-congruent and length-congruent with said focusing lens. The outer radius of this third hollow cylinder serves as the receptacle for the Fresnel lens, whose flexibility calls for a stiff element as the shaping contact surface. The lens formed by the smooth-walled, unstructured third hollow cylinder scatters the light beams of the illumination means to a small extent in the horizontal direction and, thanks to the superimposition of the elementary cone of light rays, accounts for a more uniform illumination inside the ring lamp.

An embodiment of the ring lamp according to the invention may also have the light source and the lens system enclosed in a pressure-proof housing consisting of an outer and an inner cylindrical wall as well as a top and bottom annular cover, each having an opening, so that the interior of the innermost other lens configured as the third hollow cylinder remains free. This creates the prerequisite for its use underwater. The sensitive electrical parts are effectively protected against seawater and the flow channel remains free inside the ring lamp where the disk of light is generated and the objects to be imaged can move unimpeded. It is likewise advantageous if the outer cylindrical wall is formed by the light source configured as a hollow cylinder, and the inner cylindrical wall is formed by the other focusing lens configured as the third hollow cylinder. In this case, the hollow cylinder that forms the light source is delimited by a cylindrical, pressure-proof outer wall on whose inside the light diodes are arranged. The outer radius of the other hollow cylinder forming the Fresnel lens demarcates the inner radius of the light source.

The third hollow cylinder forming the other lens, which accommodates the Fresnel lens on its outer radius, may be designed as a pressure-proof inner wall of the housing and, with its inner radius, at the same time defines the inner radius of the housing and thus of the ring lamp. Pressure-proof covers configured as rings with an opening and arranged on the top and bottom ends of the hollow cylinders complete the housing, thus defining the overall dimensions of the ring lamp. The outer radii of the covers correspond to the outer radius of the light source, while the inner radii of the covers correspond to the inner radius of the other lens. In this manner, the interior of the ring lamp with the disk of light is open to the current and the light source is protected against the effects of the flowing medium. As protection against the penetration of water, especially at great depths, the covers have to be sealed off against the outer and inner cylindrical walls. An aperture diaphragm is recommended for purposes of greater control of the light emission in order to attain a low-scatter, defined disk of light. The sealing of the cover and the aperture diaphragm can be combined in a particularly advantageous manner if the aperture diaphragm is configured as an O-ring gasket that is adjacent to the annular cover and that is sunk as an inner wall into the ends of the third hollow cylinder that forms the other focusing lens, as a result of which said O-ring gasket is located in the optical path of the light source and of the lens system. Mainly round gaskets, that is to say, O-rings, inserted in matching grooves, are suitable for use as simple sealing systems that can be adapted to any external pressure and that serve as an aperture diaphragm. These O-rings allow the pressure-proof housing to be easily opened and closed for maintenance purposes, they are inexpensive and their conditions of use are generally known.

An embodiment of the ring lamp according to the invention may include the outer radius of the pressure-proof housing being within a range from 100 mm to 150 mm and its inner radius being within a range from 40 mm to 60 mm and the length of the hollow cylinders that form the light source and the lens system does not amount to more than 10 mm and the total length of the ring lamp does not exceed 40 mm. These are only examples of dimensions, but their mention should in no way whatsoever restrict the general use of the ring lamp according to the invention in any other dimensions.

For underwater use, and optionally at great depths, a high yield of light at a high degree of efficiency is needed, in other words, a long battery life as well as low heat generation at the light source. Therefore, the illumination means may be light diodes. Light diodes have a high efficiency and an excellent service life. Therefore, they only generate low amounts of dissipation heat and have an operational life that regularly exceeds the useful life of the other components. Light diodes are small in size and a plurality of them can be arranged very close to each other so as to form the light source. Owing to their small diameter, the cylinder created can be of a very small height, such as can be required, for example, for a VPR for small plankters and slow flow rates or else for a highly sensitive camera. Only since the industry has been able to provide light diodes having a great brightness have applications such as the ring lamp described here become technically possible in the first place as well as economically feasible. Other illumination means may deliver a luminous flux that is either too weak or energetically ineffective (discharge lighting, incandescent light) or else may have insufficient illumination (laser light). The spectrum of the light emitted by the light diodes depends on the task envisaged for the ring lamp. In the standard case, it can be white light, whose spectral distribution only plays a subordinate role when it comes to simple imaging. Therefore, for many examinations, this can be light having a precisely determined spectrum or it can be light having individual spectral colors.

When light diodes are used as illumination means in the light source, they can be arranged with their longitudinal axis directly in the direction of emission, in other words, perpendicular to the axis of the hollow cylinder that forms the light source. Due to the lengthwise extension of the light diodes, the outer diameter of the ring lamp and thus the dynamic pressure generated in the water currents then become correspondingly large. However, in an embodiment of the ring lamp according to the invention the light source may have an illumination means that emits light in the direction of the axis of the hollow cylinder that forms the light source, as well as a circumferential deflection mirror arranged at an angle of 45°. The light diodes can then be arranged with their longitudinal axis parallel to the axis of the hollow cylinder and thus the outer diameter of the ring lamp can be reduced. The circumferential mirror deflects the light by 90° into the requisite light emission direction perpendicular to the axis of the hollow cylinder. Therefore, the length of the emitting surface no longer corresponds to the length of the hollow cylinder that forms the light source, but rather only to the length of the projection surface of the mirror. For this reason, the latter is selected in accordance with the desired thickness of the disk of light. This arrangement causes the length of the ring lamp to be somewhat larger but with a reduced outer diameter that is thus more favorable in terms of the current. In this arrangement, the curved mirror functions as a lightweight hollow mirror, so that the fanned-out light beams coming from the illumination means are more favorably deflected in the direction of the center axis of the hollow cylinder.

FIG. 1 shows a top view of a ring lamp RL without the top cover DO, which can possibly be used in a video plankton recorder. The light source LQ, which is configured as a hollow cylinder H1, is arranged all the way on the outside. The outer contour A1 of the light source at the same time demarcates the outer edging AG of the pressure-proof housing DG that encloses the ring lamp RL. Its inner contour I1 is at the same time the outer contour A2 of the other hollow cylinder H2 that forms a focusing lens LE. The one focusing lens LE is configured as a flexible Fresnel lens FL. The inner counter 12 of the Fresnel lens FL configured as a hollow cylinder H2 firmly lies against the outer contour A3 of the hollow cylinder H3 that forms the other focusing lens LW. The other focusing lens LW is a simple, unstructured element whose inner contour 13 at the same time forms the inner edging IG of the pressure-proof housing DG that encloses the ring lamp RL. The Fresnel lens FL and the other lens LW together form the lens system LY. The top and bottom covers DO, DU (not shown here), each of which have an opening OE having the size of the inner radius 13 of the housing DG, complete the pressure-proof housing DG. The interior IB of the ring lamp RL, which is located inside the inner edging IG of the pressure-proof housing DG, remains open at its ends and constitutes the flow channel SK illuminated by the light source LQ that serves to observe and image objects passing through. The light source LQ has light diodes LD as the illumination means LM. The light diodes LD are uniformly distributed on an intermediate radius ZR of the light source LQ configured as a hollow cylinder H1, which at the same forms the inner edging of the outer wall WA of the pressure-proof housing DG that encloses the ring lamp RL. The light LL emitted by the light diodes LD traverses the air space LR in the hollow cylinder H1, is picked up by the Fresnel lens FL and focused onto the center ZB of the ring lamp RL. The light LL is further compacted by the other lens LW that forms the inner wall WI of the housing DG and that has a biconvex form. At the inner contour 13 of the other lens LW, the light LL finally enters the interior IB of the ring lamp RL and, due to multiple reflections, spreads uniformly in the radial plane RE on the opposite wall of the other lens LW. The walls WA, WI of the housing DG have screw holes SL by means of which they are screwed to the covers DO, DU so as to complete the housing DG. In order to protect the light diodes LD against moisture and the penetration of pressurized water or any liquids or gases under variable pressure conditions, O-ring gaskets OD are provided between the walls WA, WI and the covers DO, DU. These gaskets fit into grooves ON that have been made into the walls WA, WI. The O-ring gaskets OD in the inner wall WI at the same time serve as annular aperture diaphragms AB arranged in the center of the optical path behind the one focusing lens LE for the light LL that illuminates the delimited volume BV and so further reduce the light scatter outside of the disk of light LS for which the drawing plane at the same time constitutes the radial plane RE.

Figure 2:
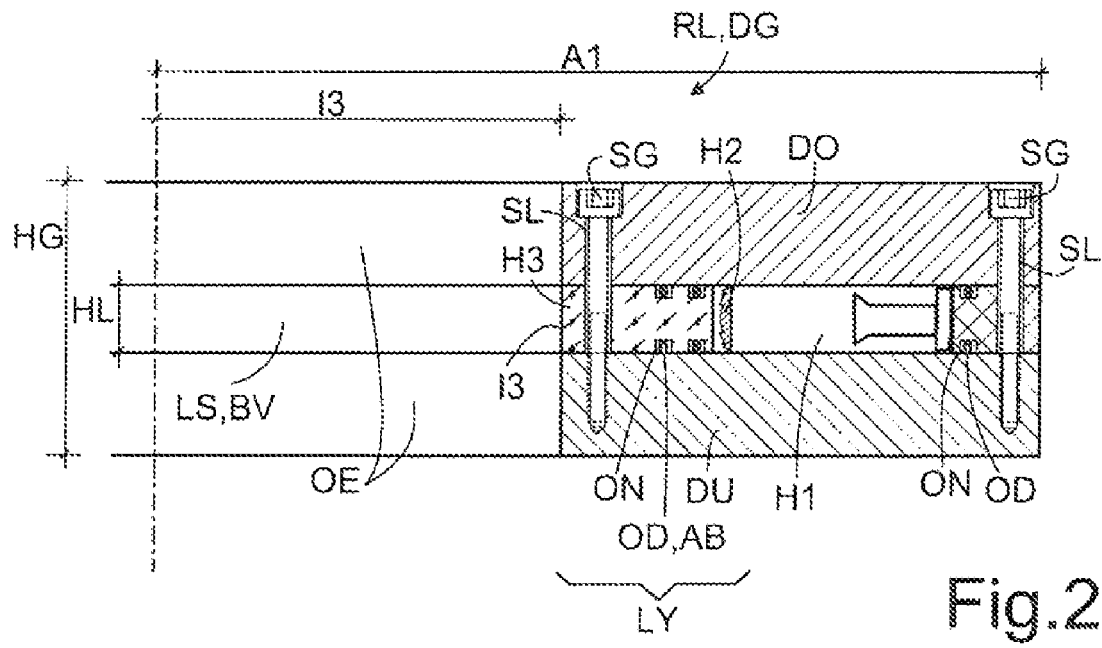
FIG. 2 shows a sectional view along the X-X marking in FIG. 1.

FIG. 2 depicts a sectional view along the line X-X in FIG. 1. Any reference symbols not shown here can be found in FIG. 1. It also shows the top and bottom covers DO, DU with their openings OE which, with the screws SG inserted into the screw holes SL, secure the pressure-proof housing DG. This figure also shows the arrangement of the O-ring gaskets OD that fit into the grooves ON of the other focusing lens LW of the lens system LY and of the outer wall WA and, on the one hand, protect the interior of the light source LQ against the penetration of water and, on the other hand, as aperture diaphragms AB, restrict the light LL to the disk of light LS and thus to the delimited volume BV, and reduce the scatter. In the case of short hollow cylinders H1, H2, H3, the total length HG of the ring lamp RL and thus the length HL of the disk of light LS are small.

As an example with actual numbers, an outer radius A1 ranging from 100 mm to 150 mm, an inner radius 13 ranging from 40 mm to 60 mm, a total length $HG \leqq 40$ mm and a length HL of the disk of light $LS \leqq 10$ mm are mentioned. Other dimensions are likewise possible.

Figure 3:
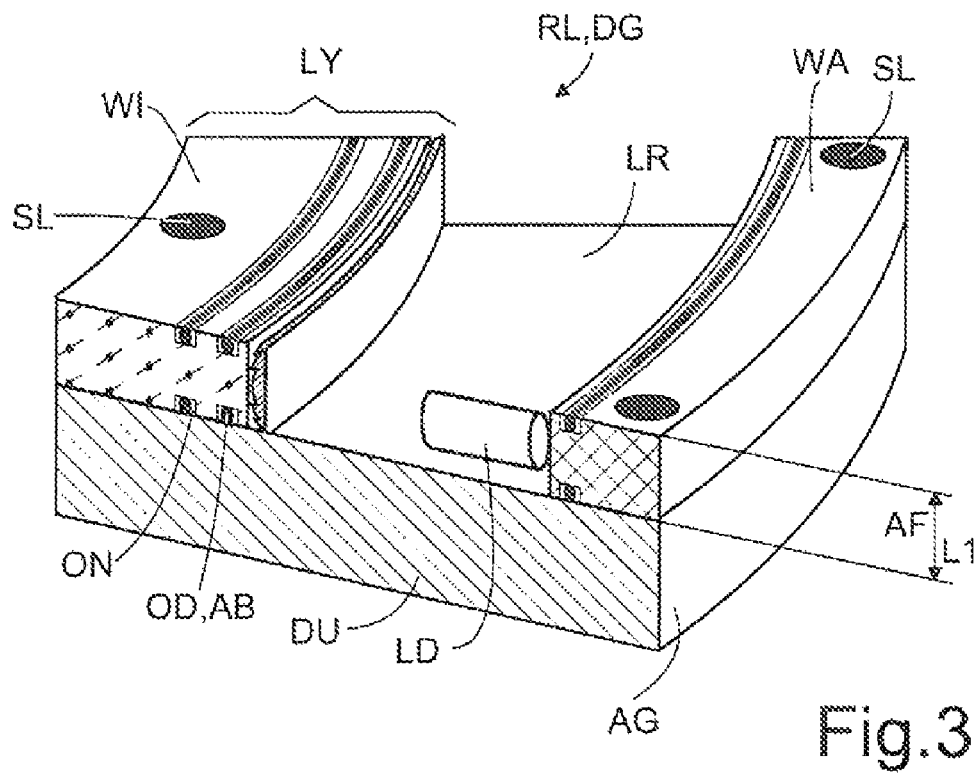
FIG. 3 shows a perspective view of a section of the ring lamp according to FIG. 1.

FIG. 3 shows a perspective view of a section of the ring lamp according to FIG. 1. It serves to further illustrate the structure of the ring lamp RL and shows the height of the emitting surface AF which, in this design, corresponds to the length L1 of the hollow cylinder H1. This figure essentially shows the grooves ON with the O-ring gaskets OD that function as aperture diaphragms AB in the walls WA, WI as well as the arrangement of the screw holes SL outside of the O-ring gaskets OD relative to the air space LR.

Figure 4:
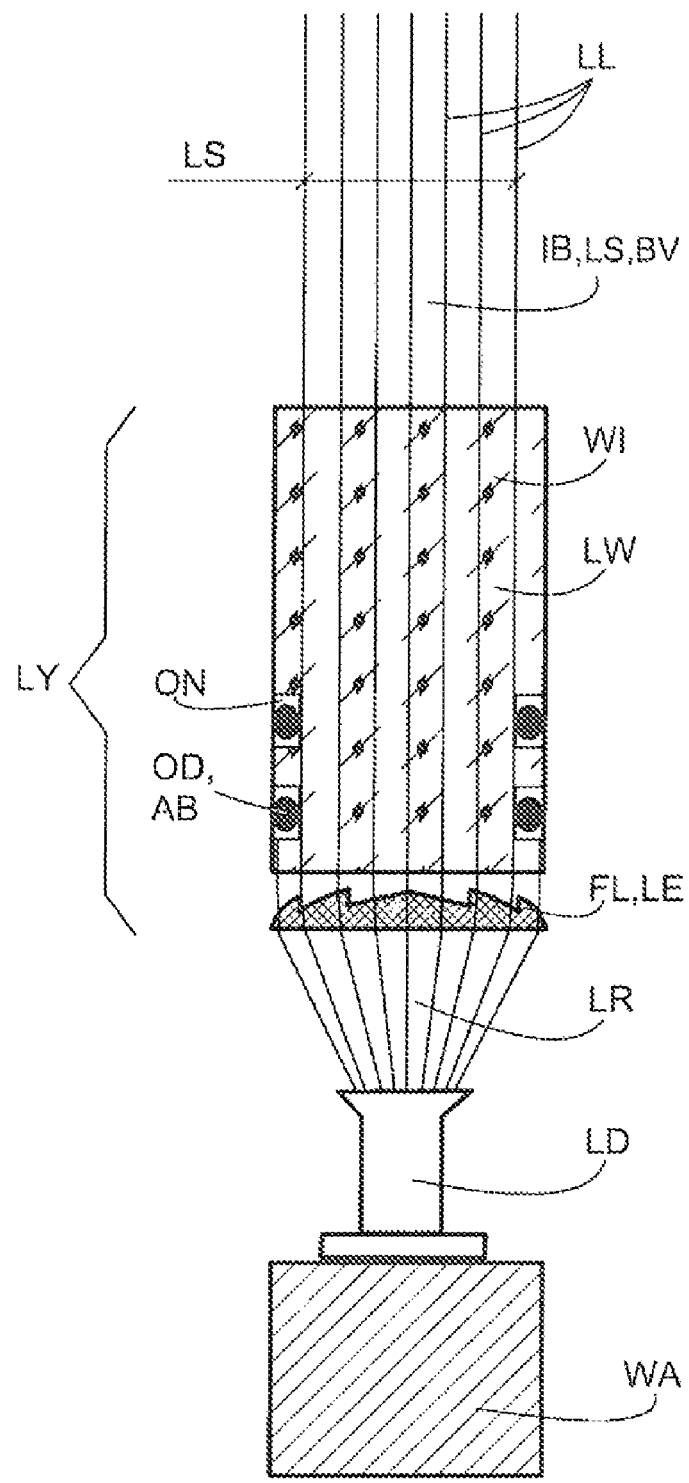
FIG. 4 shows the optical path of the ring lamp according to FIG. 1.

FIG. 4 shows the optical path of the light LL leading from the light diode LD onto the outer wall WA through the air space LR through the lens system LY with the one focusing lens LE that is configured as a Fresnel lens FL, and the other focusing lens LW configured as a simple, unstructured body, to the interior IB of the ring lamp RL. The influence of the O-ring gasket OD in the grooves ON as the aperture diaphragm AB is clearly shown here.

Figure 5:
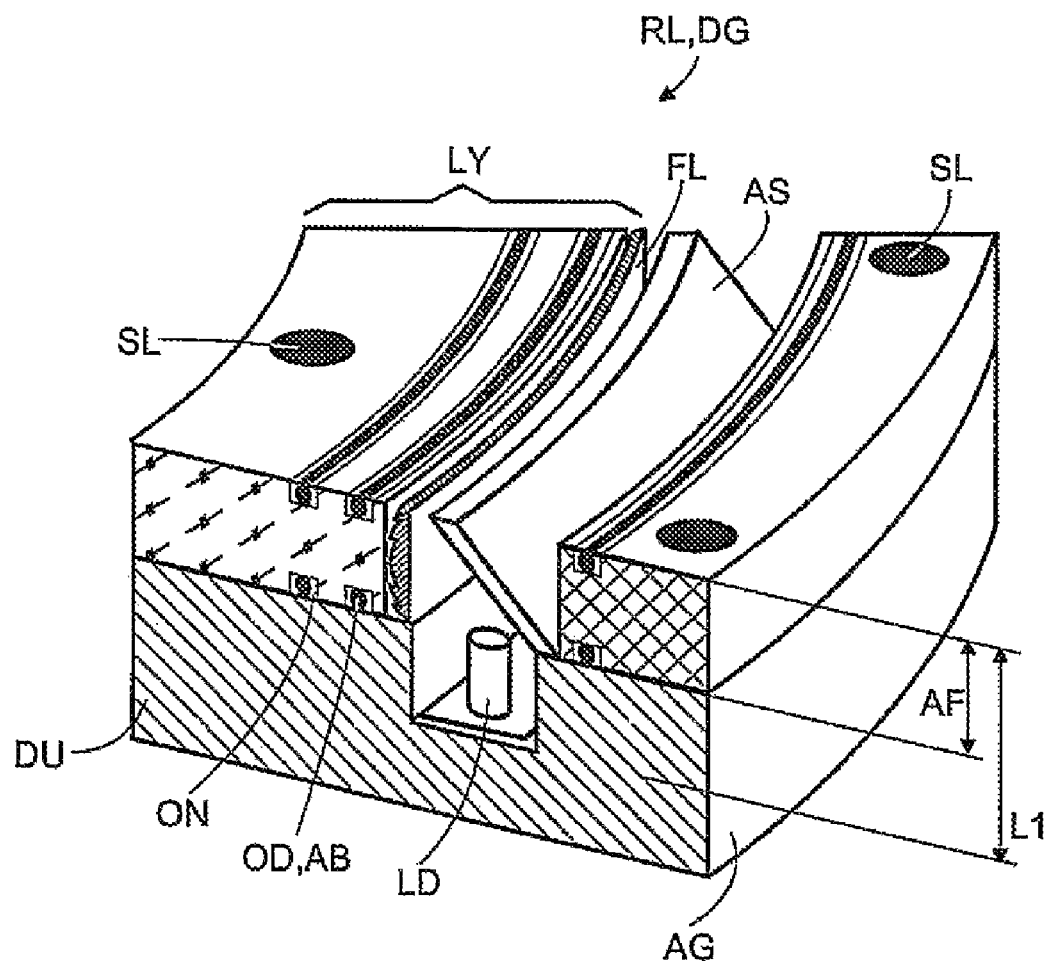
FIG. 5 shows an embodiment of the ring lamp with a 45° deflection mirror.

FIG. 5 shows an embodiment of the ring lamp with a 45° deflection mirror. In this variant, the ring lamp RL has a reduced outer diameter but a greater length than in FIG. 2. This is achieved through the orientation of the light diodes LD parallel to the center axis of the hollow cylinder H1 that forms the light source LQ and through the arrangement of a circumferential deflection mirror AS at an angle of 45°. The length L1 of the hollow cylinder H1 that forms the light source LQ is increased by this measure, but the outer diameter of the ring lamp RL on the outer edging AG is considerably reduced and consequently the flow properties are improved. Owing to the curvature of its circular shape, the deflection mirror AS functions as a hollow minor and has the effect of focusing the fanned-out light beam of the light diode LD.

LIST OF REFERENCE SYMBOLS

A1 outer radius H1
A2 outer radius H2
A3 outer radius H3
AB aperture diaphragm
AF emitting surface
AG outer edging
AS deflection mirror
BV delimited volume
DG pressure-proof housing
DO top cover
DU bottom cover
FL Fresnel lens
H1 hollow cylinder that forms the LQ
H2 other hollow cylinder
H3 third hollow cylinder
HL total length
HL length LS
I1 inner radius H1
I2 inner radius H2
I3 inner radius H3
IB interior
IG inner edging
L1 length of H1
LD light diode
LE focusing lens
LL light
LM illumination means
LQ light source LR air space
LS disk of light
LW other focusing lens
LY lens system
OD O-ring gasket
OE opening
ON groove
RE radial plane
RL ring lamp
SG screw
SK flow channel
SL screw holes
WA outer wall DG
WI inner wall DG
ZB center
ZR intermediate radius

The invention claimed is:

1. A ring lamp comprising:
a light source including a first hollow cylinder with a lighting device disposed therein, the light source having an emitting surface with a light-emitting direction oriented toward an axis of the hollow cylinder;
a light directing device configured to direct light emission, the light directing device including a lens system including at least one lens having a form of a second hollow cylinder and configured to focus light into a radial plane which is orthogonal to the axis, the lens system including a ring-shaped aperture diaphragm disposed in an optical path of the light emission behind the at least one lens,
wherein the emitting surface of the light source and the lens system have a same axial length, are coaxial and axially aligned with each other, and
wherein a radial surface defined by an inner radius of the lens system and the length of the lens system span a delimited volume.

2. The ring lamp as recited in claim 1 wherein the at least one lens includes a Fresnel lens.

3. The ring lamp as recited in claim 2 wherein the Fresnel lens includes a flexible film.

4. The ring lamp as recited in claim 3 wherein the lens system includes a second focusing lens having a form of a third, smooth-walled, unstructured hollow cylinder, the second focusing lens having a same axial length as the at least one focusing lens and being disposed coaxially with and axially aligned with the at least one focusing lens.

5. The ring lamp as recited in claim 3 wherein the lighting device includes light diodes.

6. The ring lamp as recited in claim 2 wherein the light source includes a circumferential deflection mirror arranged at an angle of 45° to the axis.

7. The ring lamp as recited in claim 3 wherein the light source includes a circumferential deflection mirror arranged at an angle of 45° to the axis.

8. The ring lamp as recited in claim 2 wherein the lens system includes a second focusing lens having a form of a third, smooth-walled, unstructured hollow cylinder, the second focusing lens having a same axial length as the at least one focusing lens and being disposed coaxially with and axially aligned with the at least one focusing lens.

9. The ring lamp as recited in claim 2 wherein the lighting device includes light diodes.

10. The ring lamp as recited in claim 1 wherein the lens system includes a second focusing lens having a form of a third, smooth-walled, unstructured hollow cylinder, the second focusing lens having a same axial length as the at least one focusing lens and being disposed coaxially with and axially aligned with the at least one focusing lens.

11. The ring lamp as recited in claim 10 wherein the lighting device includes light diodes.

12. The ring lamp as recited in claim 1 further comprising a pressure-proof housing, the light source and the lens system being enclosed in the pressure-proof housing, the pressure proof housing including an outer cylindrical wall, an inner cylindrical wall, a bottom annular cover and a top annular cover, the bottom annular cover and the top annular cover each including an opening.

13. The ring lamp as recited in claim 12 wherein the outer cylindrical wall includes the light source in the form of the first hollow cylinder and the inner cylindrical wall includes the second focusing lens in the form of the third hollow cylinder.

14. The ring lamp as recited in claim 12 further comprising an aperture diaphragm configured as an O-ring gasket disposed adjacent to at least one of the annular covers and recessed as an inner wall into ends of the third hollow cylinder, and wherein the O-ring gasket is disposed in an optical path of the light source and lens system.

15. The ring lamp as recited in claim 12 wherein:
an outer radius of the pressure-proof housing is between 100 mm and 150 mm,
an inner radius of The pressure-proof housing is between 40 mm and 60 mm,
the length of the hollow cylinders forming the light source and lens system is no more than 10 mm, and
a total length of the ring lamp is no more than 40 mm.

16. The ring lamp as recited in claim 1 wherein the lighting device includes light diodes.

17. The-ring lamp as recited in claim 1 wherein the light source includes a circumferential deflection mirror arranged at an angle of 45° to the axis.

18. A particle detection system comprising:
a ring lamp comprising:
a light source including a first hollow cylinder with a lighting device disposed therein, the light source having an emitting surface with a light-emitting direction oriented toward an axis of the hollow cylinder;
a light directing device configured to direct light emission, the light directing device including a lens system including at least one lens having a form of a second hollow cylinder and configured to focus light into a radial plane which is orthogonal to the axis, the lens system including a ring-shaped aperture diaphragm disposed in an optical path of the light emission behind the at least one lens,
wherein the emitting surface of the light source and the lens system have a same axial length, are coaxial and axially aligned with each other, and
wherein a radial surface defined by an inner radius of the lens system and the length of the lens system span a delimited volume.

19. The particle detection system as recited in claim 18 wherein the particle detection system is a video plankton recorder.

* * * * *